United States Patent [19]

McKay et al.

[11] 4,003,376
[45] Jan. 18, 1977

[54] APPARATUS FOR STRAIGHTENING THE SPINAL COLUMN

[75] Inventors: Douglas William McKay, Washington, D.C.; Teddy L. Bolinger; Norman L. Emerick, both of Warsaw, Ind.

[73] Assignee: Bio-Dynamics, Inc., Indianapolis, Ind.

[22] Filed: Aug. 25, 1975

[21] Appl. No.: 607,108

[52] U.S. Cl. .............................. 128/69; 128/92 R
[51] Int. Cl.² ............................................ A61F 5/00
[58] Field of Search ............ 128/92 R, 92 A, 92 B, 128/92 D, 92 C, 69, 78, 87

[56] References Cited
UNITED STATES PATENTS

| | | | |
|---|---|---|---|
| 2,774,350 | 12/1956 | Cleveland, Jr. | 128/92 R |
| 2,825,329 | 3/1958 | Caesar | 128/92 R |
| 3,565,066 | 2/1971 | Roaf | 128/69 |
| 3,648,691 | 3/1972 | Lumb et al. | 128/92 D |
| 3,693,616 | 9/1972 | Roaf et al. | 128/69 |

*Primary Examiner*—John D. Yasko
*Attorney, Agent, or Firm*—Woodard, Weikart, Emhardt & Naughton

[57] ABSTRACT

Apparatus for straightening the spinal column. The apparatus includes an elongated member securable forwardly of and against the spinal column. A pair of fastening devices extend around the spinal column from the elongated member to a pair of bands located rearwardly of and adjacent the spinal column. The fasteners are tightened to force the bands toward the elongated member thereby causing the spinal column to straighten in the particular area. The bands are provided with handle portions removable therefrom after the bands are positioned adjacent the spinal column.

11 Claims, 9 Drawing Figures

APPARATUS FOR STRAIGHTENING THE SPINAL COLUMN

BACKGROUND OF THE INVENTION

1. Field of the Invention

This invention is in the field of medical devices and methods for correcting spinal column deficiencies.

2. Description of the Prior Art

One of the most perplexing problems to the pediatric orthopedic surgeon or spine surgeon has been paralytic kyphosis of the spine, particularly the meningomyelocele. The reason for the severe problems is the early age of onset, decubitus ulcers, inability to brace, difficulty in surgically correcting the kyphosis without substantially shortening the trunk and difficulty maintaining the correction. Kyphosis of the spine is a selfperpetuating problem. In the meningomyelocele or paralytic kyphosis the individual's paravertebral muscles are ineffectual and the abdominal muscles increase or perpetuate the kyphosis. Due to the early onset and the early fixation of the spine and perpetual pressure sores, surgeons have attempted to correct this problem early. Some have advocated removal of the apical vertebral body of the kyphosis and fusion which shortens the spine. The deformity recurs rapidly because the fusion is not long enough and does not correct the lordosis that occurs above and below the kyphosis. Thus, the spine has to be straightened from the apex of the upper lordosis to the apex of the lordosis below the kyphotic area. Due to the fact that this deformity occurs so early in life it necessitates that something be done early and the attack has to be anteriorly. The absence of posterior elements of the spine and the cancellous bone of the vertebral body makes the conventional internal fixation devices useless. Therefore, a device was designed to satisfy the following criteria: (1) Correct the deformity without shortening of the spine but depend on the ligamentus structures for support; (2) Maintain the correction until spinal fusion has occurred from the apex of the upper lordosis to the apex of the lower lordosis across the kyphosis; (3) If the soft tissue (arteries, veins or abdominal wall) will not allow immediate correction, a simple staged procedure can be used to gradually correct the kyphosis.

Some devices have been provided for straightening or supporting the spine. For example, U.S. Pat. Nos. 2,702,031 issued to H. L. Wenger and 3,242,922 issued to C. B. Thomas disclose supporting devices mountable to the pelvic bone extending upwardly to support the spinal column. Another approach has been to replace one or more natural vertebrae with an artificial device such as disclosed in U.S. Pat. No. 3,426,364 issued to W. V. Lumb. Another approach disclosed in U.S. Pat. No. 2,774,350 issued to C. S. Cleveland, Jr. provides tension to a vertebrae in order to correct the deficiency. Other devices such as disclosed in U.S. Pat. Nos. 1,950,799 issued to C. P. Jones and 3,693,616 issued to Roaf et al disclose devices for securing bones together. Another device disclosed in U.S. Pat. No. 3,565,066 issued to Robert Roaf discloses an implant for causing the displaced vertebrae to be drawn toward a rigid member. The method disclosed in U.S. Pat. No. 3,648,691 issued to William Lumb provides an appliance for use in bridging one or more diseased or damaged vertebrae.

SUMMARY OF THE INVENTION

One embodiment of the present invention is a spinal column straightener including a rigid support insertable adjacent the spinal column so as to extend lengthwise along the spinal column, the support having first and second opposite longitudinally extending edge portions and further including means extendable around the spinal column from the first to the second edge portions with the means being operable to force the support against the spinal column along the entire length of the support.

Another embodiment of the present invention is a method of straightening the spinal column including the steps of positioning a rigid elongated member adjacent the forward side of the spinal column, positioning the member to extend lengthwise along the spinal column, and forcing the spinal column against the elongated member along the entire length of the member straightening the spinal column.

It is an object of the present invention to provide a new and improved apparatus for straightening a spinal column.

A further object of the present invention is to provide a new and improved method for straightening the spinal column.

Related objects and advantages of the present invention will be apparent from the following description.

DESCRIPTION OF THE PREFERRED EMBODIMENT

Figure 2:
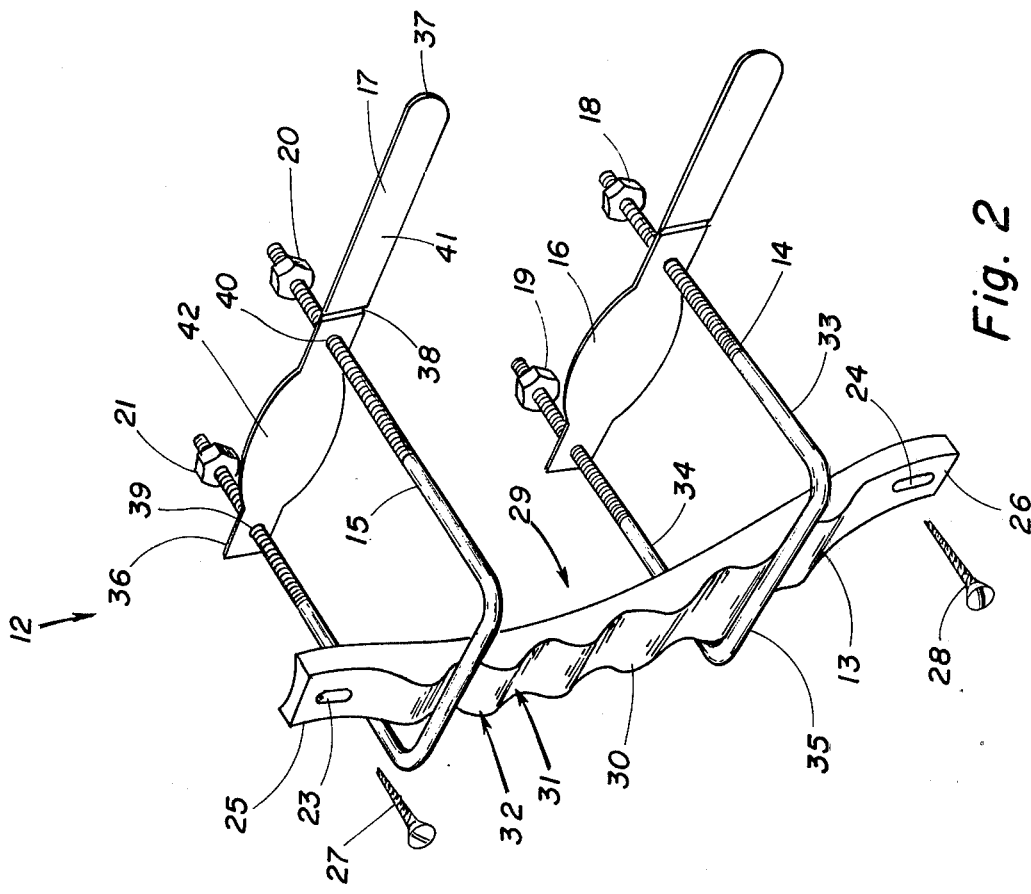
FIG. 2 is an enlarged perspective view of the plate assembly.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
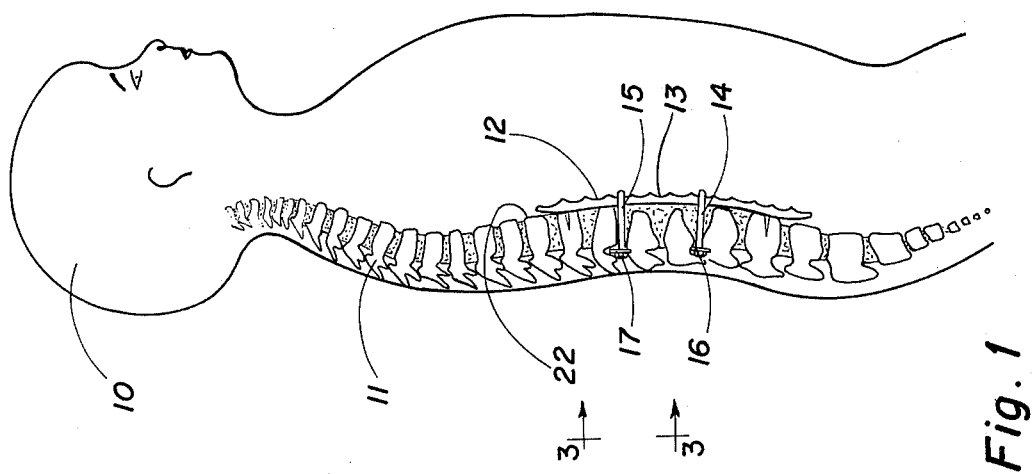
FIG. 1 is a schematic side view of a spinal column with the plate assembly incorporating the present invention attached thereto.
Figure 3:
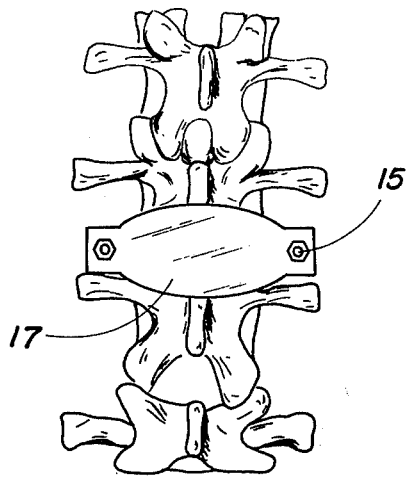
FIG. 3 is an enlarged fragmentary view looking in the direction of arrows 3—3 of FIG. 1 of the preferred embodiment of the present invention.

Referring now more particularly to FIG. 1, there is shown a human subject 10 with a spinal column 11 straightened by the apparatus 12 incorporating the present invention. Apparatus 12 includes an elongated member 13 (FIG. 2) forced against the spinal column by a pair of U-shaped bolts 14 and 15, respectively, secured to bands 16 and 17 by internally threaded nuts 18, 19, and 20, 21.

The method of straightening a spinal column includes the step of positioning member 13 adjacent the forward side 22 (FIG. 1) of spinal column 11 with member 13 extending lengthwise along the spinal column. Member 13 is essentially a straight or slightly lordotic 10 degree to 15 degree plate that attaches to the vertebral bodies anteriorly with cancellous screws to keep the plate from migrating or slipping off the vertebral bodies. A pair of slots 23 and 24 are provided respectively in the top end 25 and bottom end 26 of member 13. Bone screws 27 and 28 respectively extend through slots 23 and 24 and are threaded into the vertebral bodies. Thus, member 13 is fastened directly to the spinal column. Member 13 is rigid and has a concave configuration 29 facing the spinal column. The top end 25 and bottom end 26 flare outwardly of concave configuration 29 to insure that the ends of the member do not dig into the spinal column as the nuts 18 through 21 are tightened. The opposite surface 30 of member 13 facing away from the spinal column and forwardly of the spinal column is in contact with bolts 14 and 15. Surface 30 includes a plurality of grooves 31 and ridges 32 with each ridge having a height of approximately 1 to 1¼ centimeters. Each U-shaped bolt fits within a groove 31 thereby limiting relative motion between bolts 14 and 15 and member 13.

Bolt 14 will now be described it being understood that a similar description applies to bolt 15. Bolt 14 includes a pair of parallel rods 33 and 34 which are externally threaded so as to receive nuts 18 and 19. Rods 33 and 34 are integrally joined together perpendicularly to rod 35 which extends through one of the grooves 31. Bolts 14 and 15 in conjunction with bands 16 and 17 extend from member 13 around the spinal column and back to member 13 being operable to force the spinal column to contact member 13 along the entire length of member 13 thereby straightening the spinal column. The spinal column is forced against member 13 so as to assume the concave configuration 29 as well as to contact the flared ends 25 and 26 of member 13.

Band 17 will now be described it being understood that a similar description applies to band 16. Band 17 has a pair of opposite ends 36 and 37 with the band being of constant thickness except at groove 38 where the band is considerably weakened. A pair of holes 39 and 40 are positioned between end 36 and groove 38 to receive the opposite ends of bolt 15. The height of band 17 is likewise constant except between holes 39 and 40 where the height increases. After member 13 is fastened by screws 27 and 28 in front of and to the spinal column, bolts 14 and 15 are positioned around member 13 and likewise around the spinal column. Bands 16 and 17 are then inserted behind the spinal column with the bolts being extended through the bands and the nuts eventually being threaded onto the bolts. Groove 38 is provided so as to allow for the braking off of the portion of the band extending between groove 38 and end 37. Portion 41 of band 17 is therefore used as a handle to help the surgeon guide portion 42 of the band into the correct location behind the spinal column. Portion 41 may then be bent along groove 38 so as to break from portion 42 which remains adjacent the spinal column.

Figure 5:
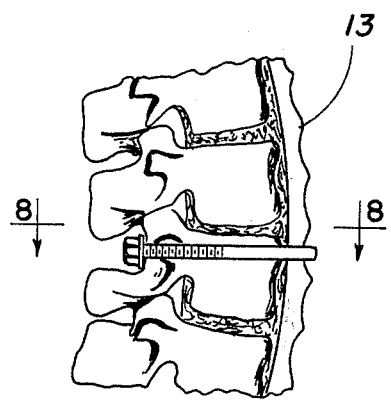
FIG. 5 is an enlarged fragmentary side view of a portion of the plate assembly mounted to the spinal column in FIG. 1.
Figure 6:
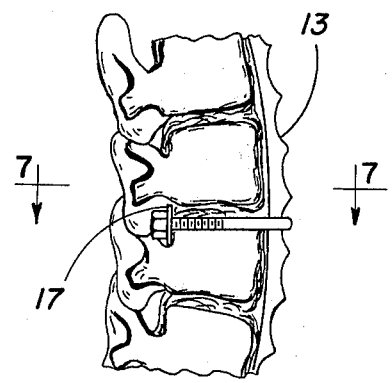
FIG. 6 is the same view as FIG. 5 only showing the band of the plate assembly located inwardly as compared to the band positioning in FIG. 5.

Member 13 extends lengthwise along the spinal column whereas bands 16 and 17 have lengths which extend across the spinal column. Bolts 14 and 15 and nuts 18 through 21 limit movement of bands 16 and 17 relative to the U-shaped bolts. Nuts 18 through 21 may be adjusted through two small posterior incisions. In those cases where there are no posterior elements such as shown in FIG. 6, the band is inserted between the intravertebral foraman posterior to the posterior longitudinal ligament and anterior to the cord if the child has function in the cord at that level or there are no posterior elements. With posterior elements, the band runs over the facet joints, the lamina, and part of the spinous process such as shown in FIG. 5. As the nuts on the U-shaped bolts are tightened from the posterior approach, the kyphosis is pulled to the plate and the lordosis is corrected by posterior thrust of the surface of the plate. The intravertebral discs are removed and the defect is grafted with cancellous bone. If the kyphosis is severe and the abdominal wall is too taunt, the patient can be closed and two or three weeks later through a small posterior incision, the nuts may be tightened slowly stretching out the abdominal wall. It is believed advisable to accomplish the above procedure when the patient is around four to six years of age. Likewise, it is advisable to put the patient in an external support until fusion has occurred.

Figure 7:
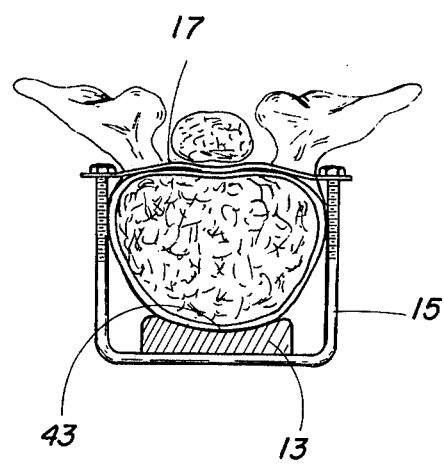
FIG. 7 is an enlarged cross-sectional view taken along the line 7—7 of FIG. 6, viewed in the direction of the arrows and rotated clockwise 90°.
Figure 8:
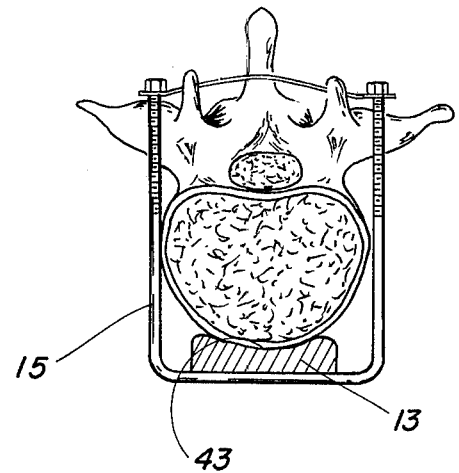
FIG. 8 is an enlarged cross-sectional view taken along the line 8—8 of FIG. 5, viewed in the direction of the arrows and rotated clockwise 90°.

FIGS. 7 and 8 are respectively cross-sectional views of the plate assembly shown in FIGS. 6 and 5. Member 13, in addition to having a concave configuration 29 (FIG. 2) which extends from the top flared out end 25 to the bottom flared out end 26, has a second concave configuration 43 (FIGS. 7 and 8) to complementarily receive the rounded configuration of the spinal column. Concave configuration 43 extends across the spinal column as compared to the concave configuration 29 which extends the length of the column. Concave configuration 43 is constant from the top end 25 to the bottom end 26 of member 13.

By tightening nuts 18 through 21, bands 16 and 17 are caused to move toward member 13. Bolts 14 and 15 extend not only across surface 30 of member 13 but likewise extend from the longitudinally extending edge portions of member 13 and outwardly of the spinal column to bands 16 and 17.

Figure 4:
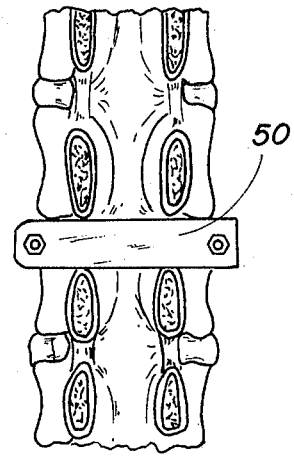
FIG. 4 is the same view as FIG. 3 only showing an alternative embodiment of the plate assembly.

In the alternate embodiment of the band shown in FIG. 4, band 50 is identical to bands 16 and 17 with the exception that band 50 has a uniform height from one end of the band to the opposite end of the band. Likewise, band 50 is provided with a groove enabling the handle portion to be broken off of the band after the band is inserted behind the spinal column. Band 50 is shown in FIG. 4 with the handle portion removed therefrom. Many other variations are contemplated and included in the present invention. For example, in one embodiment, member 13 was not provided with a concave configuration 29 but instead was flat. Another variation contemplated and included herein is the addition of clamps mounted to surface 30 of member 13 with surface 30 being smooth. Bolts 14 and 15 are then attached to member 13 by the clamps mounted thereon preventing relative motion between member 13 and bolts 14 and 15.

Figure 9:
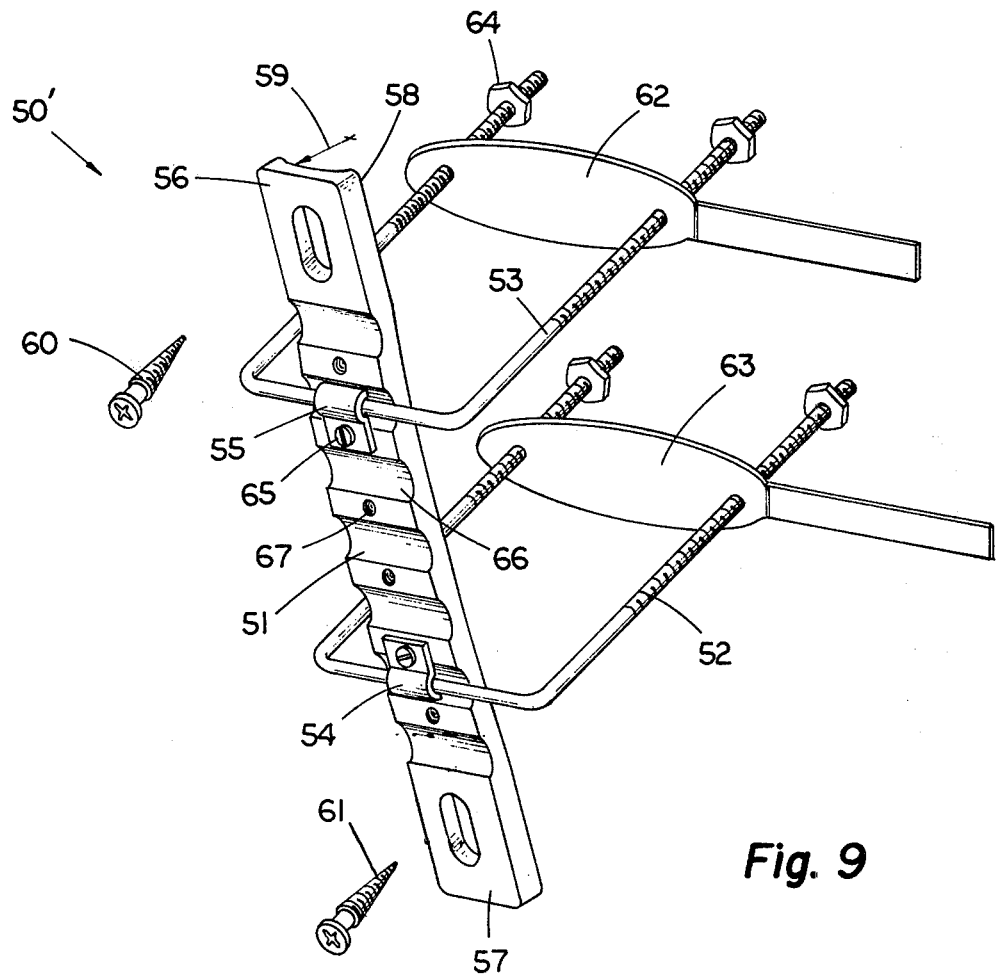
FIG. 9 is a perspective view of another embodiment of the plate assembly incorporating the present invention.

Another embodiment of the apparatus for straightening the spinal column is shown in FIG. 9. Apparatus 50 is identical with apparatus 12 previously described except that the elongated member 51 is flat and does not include the concave configuration 29 of apparatus 12. In addition, the pair of U-shaped bolts 52 and 53 are secured to the elongated member 51 by a pair of clamps 54 and 55.

The top end 56 and bottom end 57 of elongated member 51 do not flare outwardly as described for apparatus 12. Surface 58 of elongated member 51 is provided with a concave configuration 59 similar to concave configuration 43 of apparatus 12 (FIG. 7). Elongated member 51 is attached to the spine with bone screws 60 and 61 in the manner identical to apparatus 12. Likewise, bands 62 and 63 are positioned on rods 52 and 53 and secured thereby by conventional hexagonally shaped nuts 64 in a manner identical to that described for apparatus 12. Clamps 54 and 55 are secured to the elongated member 51 by screws 65 and are held in grooves 66 by the clamps. Additional holes 67 are provided in the elongated member for receiving screws 65 in the event that the clamps are to be moved to adjacent grooves 66. Clamp 55 prevents the slippage of the U-shaped bolts before and after insertion. Clamps 54 and 55 may also be mounted to member 13 for holding bolts 14 and 15.

While the invention has been illustrated and described in detail in the drawings and foregoing description, the same is to be considered as illustrative and not restrictive to character it being understood that only the preferred embodiments have been shown and described and that all changes and modifications that come within the spirit of the invention are desired to be protected.

The invention claimed is:

1. A device for straightening the spinal column comprising:
    an elongated first member with length insertable forwardly of and adjacent the spinal column so as to extend lengthwise along said spinal column;
    first means operable to attach said member to said spinal column limiting relative motion between said member and said spinal column; and,
    second means extendable from said member around said spinal column and back to said member being operable to force said spinal column to contact said member along said length of said member straightening said spinal column.

2. The device of claim 1 wherein:
said elongated member is rigid with a concave configuration facing said spinal column.

3. The device of claim 2 wherein:
said first means includes at least one cancellous screw extendable through said member and into said spinal column.

4. The device of claim 2 wherein:
said elongated member has a top end and a bottom end flared outwardly of said concave configuration to insure said top end and bottom end will not dig into said spinal column as said second means is tightened.

5. The device of claim 1 wherein:
said second means includes:
a second elongated member with length insertable rearwardly of and adjacent said spinal column so as to extend lengthwise across said spinal column and, further includes;
a first threaded fastener extending outwardly of said spinal column and connecting and forcing said first member to said second member.

6. The device of claim 5 wherein:
said second means includes;
a third elongated member with length insertable rearwardly of and adjacent said spinal column so as to extend lengthwise across said spinal column and further includes;
a second threaded fastener extending outwardly of said spinal column and forcing said first member to said third member.

7. The device of claim 5 wherein:
said first threaded member includes a U-shaped bolt with opposite threaded ends extending through said second elongated member, said second means further includes a pair of internally threaded elements threadedly receiving said opposite threaded ends limiting movement of said second member relative to said U-shaped bolt.

8. The device of claim 7 wherein:
said first member has a forwardly facing surface in contact with said U-shaped bolt, said forwardly facing surface has a groove provided thereon to limit relative motion between said U-shaped bolt and said first member.

9. A spinal column straightener comprising:
a rigid support insertable adjacent the spinal column so as to extend lengthwise along said spinal column, said support having first and second opposite longitudinally extending edge portions; and,
means extendable around said spinal column from said first to said second edge portions, said means being operable to force said support against said spinal column along the entire length of said support.

10. The spinal column straightener of claim 9 wherein:
said means includes a plurality of elements placed adjacent said spinal column oppositely of said support and further includes a plurality of fasteners securing and forcing said elements to said support.

11. The spinal column straightener of claim 10 wherein:
said fasteners include a plurality of U-bolts abuttingly engaged with said support and fastened to said elements.

* * * * *

UNITED STATES PATENT AND TRADEMARK OFFICE
CERTIFICATE OF CORRECTION

PATENT NO. : 4,003,376
DATED : January 18, 1977
INVENTOR(S) : Douglas McKay, Norman L. Emerick and Teddy L. Bolinger It is certified that error appears in the above-identified patent and that said Letters Patent are hereby corrected as shown below:

In column 3 line 34 "1 1/4" should be --1 1/2--

In column 3 line 67 "braking" should be --breaking--

In column 5 line 4 "50" should be --50'--

Signed and Sealed this

Twelfth Day of April 1977

[SEAL]

Attest:

RUTH C. MASON
*Attesting Officer*

C. MARSHALL DANN
*Commissioner of Patents and Trademarks*